(12) United States Patent
Van Antwerp et al.

(10) Patent No.: US 6,734,162 B2
(45) Date of Patent: May 11, 2004

(54) MIXED BUFFER SYSTEM FOR STABILIZING POLYPEPTIDE FORMULATIONS

(75) Inventors: William Peter Van Antwerp, Valencia, CA (US); Poonam S. Gulati, La Canada, CA (US)

(73) Assignee: MiniMed Inc., Northridge, CA (US)

( * ) Notice: Subject to any disclaimer, the term of this patent is extended or adjusted under 35 U.S.C. 154(b) by 114 days.

(21) Appl. No.: 09/733,738

(22) Filed: Dec. 8, 2000

(65) Prior Publication Data

US 2001/0031726 A1 Oct. 18, 2001

Related U.S. Application Data (60) Provisional application No. 60/177,897, filed on Jan. 24, 2000.

(51) Int. Cl.[7] .............................................. A61K 38/16
(52) U.S. Cl. .................. 514/2; 514/3; 514/4; 530/303; 530/304
(58) Field of Search .................. 514/2–4; 530/303, 530/304

(56) References Cited

U.S. PATENT DOCUMENTS

| | | | |
|---|---|---|---|
| 4,839,341 A | * 6/1989 | Massey et al. .................. | 514/4 |
| 5,474,978 A | 12/1995 | Bakaysa et al. ................ | 514/4 |
| 5,952,297 A | 9/1999 | De Felippis et al. ............ | 514/3 |
| 6,133,229 A | 10/2000 | Gibson et al. .................. | 514/2 |
| 6,174,856 B1 | 1/2001 | Langballe et al. .............. | 514/4 |

FOREIGN PATENT DOCUMENTS

| | | |
|---|---|---|
| EP | 0 726 075 A1 | 8/1996 |
| EP | 0 925 792 A2 | 6/1999 |
| EP | 1 090 640 A2 | 4/2001 |
| WO | WO98/56406 | 12/1998 |
| WO | WO99/64589 | 12/1999 |

OTHER PUBLICATIONS

Brange J. et al., "Chemical stability of insulin: 3. Influence of excipients, formulation, and pH", Acta Pharmaceutica Nordica, 4(3), 1992, pp. 149–158, XP–000990198.

Quinn R. et al., "Minimizing the Aggregation of Neutral Insulin Solutions", Journal of Pharmaceutical Sciences, vol. 72, No. 12, Dec. 1983, pp. 1472–1473, XP002913498.

* cited by examiner

*Primary Examiner*—Robert A. Wax
*Assistant Examiner*—David Lukton
(74) *Attorney, Agent, or Firm*—Gates & Cooper LLP (57) ABSTRACT

The present invention is a pharmaceutical composition for polypeptide which are not stably soluble. A preferred polypeptide is monomeric insulin and a preferred formulation consists of a TRIS-phosphate combination buffer, zinc; a phenolic preservative and an isotonicity agent such as glycerol.

7 Claims, 4 Drawing Sheets

MIXED BUFFER SYSTEM FOR STABILIZING POLYPEPTIDE FORMULATIONS

This application claims the benefit of U.S. provisional patent application serial No. 60/177,897, filed Jan. 24, 2000. The entire content of this provisional patent application is incorporated herein by reference.

BACKGROUND OF THE INVENTION

1. Field of the Invention

The present invention relates generally to pharmaceutical compositions and more specifically to improved formulations for use with therapeutic polypeptides.

2. Description of Related Art

Advances in genetic engineering technologies have made a wide variety of biologically active polypeptides available in sufficiently large quantities for use as drugs. Such polypeptides, however, can lose biological activity by a variety of chemical and physical means including deamidation, aggregation and denaturation. Consequently, the identification of buffer systems that stabilize these agents is essential for the optimization of their therapeutic benefits.

Stable formulations of therapeutic agents are particularly important for use in delivery devices that expose these agents to elevated temperatures and/or mechanical stress. Stable insulin formulations, for example, are required for use in continuous infusion systems and related devices. In continuous infusion systems, a fluid containing a therapeutic agent is pumped from a reservoir, usually to a subcutaneous, intravenous, or intraperitoneal depot. Formulations of polypeptides such as monomeric insulin analogs for use in continuous infusion systems must remain soluble and substantially free of aggregation, even though subjected to the patient's body heat and motion for periods ranging from a few days to several months. In this context, instability is promoted by the higher protein concentrations that are desirable for continuous infusion systems and by the thermo-mechanical stress to which formulations are exposed in continuous infusion systems. Therefore, improvement in the physical and chemical stability of concentrated insulin analog formulations is urgently needed to facilitate their use in continuous infusion systems. In particular, insulin formulations for implantable pump use must possess chemical and physical stability in the harsh environment of the implantable pump. The formulations must be stable during long term (90 days) storage at elevated temperature (37–40° C.) with constant agitation on a relatively hydrophobic surface (e.g. $TiO_2$ with an average contact angle of more than 60°).

As noted above, monomeric insulin analog formulations have a propensity to aggregate and to become unstable when exposed to thermo-mechanical stress. Aggregation may even be manifested as precipitation of higher-order insulin species. In this way, aggregation can prevent reproducible delivery of effective therapeutic doses of monomeric insulin analogs, and may also cause irritation at the administration site or more systemic immunological response. Consequently, insulin analog formulations stabilized against aggregation are desirable.

While a number of aqueous formulations which stabilize polypeptide compositions have been identified in the art, the destabilization of polypeptides in solution continues to create problems for medical practitioners. Consequently, there is a need for new pharmaceutical compositions which overcome the problems of the prior art. This need is fulfilled by the invention that is described below.

SUMMARY OF THE INVENTION

The present invention is a pharmaceutical composition that enhances the stability of polypeptides in an aqueous medium. Typically the composition includes a polypeptide that is prone to aggregation stabilized by a mixed buffer system. The invention relates to the discovery that a mixed TRIS buffer system provides improvements in the stabilization of polypeptides by inhibiting the aggregation of polypeptide pharmaceuticals. Specifically, by using TRIS to supply the negative coefficient of pH in combination with buffering molecules that: (1) can react with $CO_2$ and (2) have no free amine group, a formulation that provides enhanced polypeptide stability is obtained. In typical illustrative embodiments of the invention for example, one can use TRIS with acetate, phosphate or citrate buffers at the appropriate pH.

The invention described herein has a variety of embodiments. An illustrative embodiment consists of a solution formulation comprising including a physiologically tolerated mixed buffer system comprising TRIS combined with a buffering molecule which both reacts with carbon dioxide; and does not contain a free amine group, a polypeptide, zinc; and a phenolic preservative. In a preferred embodiment of the invention the buffering molecule is selected from the group consisting of acetate, phosphate and citrate. In a highly preferred embodiment, the buffering molecule is phosphate. In a related embodiment of this invention, the formulation further comprises an isotonicity agent and the polypeptide is a monomeric insulin analog selected from the group consisting of LysB28ProB29-human insulin and AspB28 human insulin.

In a specific embodiment of the mixed buffer system described herein, TRIS is present at a concentration of about 1.5 mg/ml to about 4.5 mg/ml; phosphate is present at a concentration of about 0.2 mg/ml to about 2.5 mg/ml, insulin is present at a concentration of about 250 to about 1000 U/ml, zinc is present at a concentration of about 0.07 $\mu$g/ml to about 0.09 $\mu$g/ml, m-cresol is present at a concentration of about 2.2 mg/ml, phenol is present at a concentration of about 0.9 mg/ml and glycerol is the isotonicity agent and is present at a concentration of about 16 mg/ml. In a preferred embodiment, TRIS is present at a concentration of about 2 mg/ml to about 3 mg/mil and phosphate is present at a concentration of about 0.5 mg/ml to about 1.5 mg/ml.

Yet another embodiment of the invention consists of a stable, soluble formulation of a monomeric insulin analog for use in a continuous infusion system, comprising: an isotonicity agent; a mixed buffer system consisting essentially of TRIS combined with a buffer selected from the group consisting of phosphate buffer, acetate buffer and citrate buffer; a monomeric insulin analog; zinc; and a phenolic preservative.

Yet another embodiment of the invention consists of a method for treating diabetes comprising administering an effective dose of the above-mentioned formulation to a patient in need thereof. A related embodiment of the invention consists of a method for treating hyperglycemia comprising administering an effective dose of the formulation to a patient in need thereof. In a preferred embodiments of these methods, the formulation is administered using a continuous infusion system Another embodiment of the invention disclosed herein includes a process for preparing the formulation by combining a physiologicaliy-tolerated mixed buffer system comprising TRIS combined with a buffer selected from the group consisting of phosphate buffer, acetate buffer and citrate buffer; with a polypeptide prone to aggregation; zinc; and a phenolic preservative. Yet another embodiment of the invention is a method of stabilizing a polypeptide prone to aggregation comprising combining the peptide with a physiologically-tolerated mixed buffer system comprising TRIS mixed with a buffering molecule that does not contain a free amine group and which absorbs carbon dioxide and counteracts the effects of this molecule on pH; zinc; and a phenolic preservative.

DETAILED DESCRIPTION OF THE INVENTION

The present invention provides improved methods and materials for maintaining the stability of polypeptide pharmaceuticals and preventing aggregation of such biologically active polypeptides. While specific embodiments of the invention are directed to stabilization of insulin and its analogs, polypeptides which are particularly susceptible to denaturation and aggregate formation, the utility of the invention extends generally to all protein and polypeptide pharmaceuticals. Polypeptides suitable for use in the practice of the present invention include, for example, insulin and it analogs (e.g. LysB28ProB29-human insulin and AspB28 human insulin), interleukins (e.g. IL-2 and its analogs), interferons including β-interferon (IFN-β and its analogs such as IFN-$\beta_{ser17}$), as described in EPO 185459B1 (incorporated herein by reference), hGH, and other polypeptides that are prone to aggregation in solution.

Typically, the mixed buffer system disclosed herein is used with polypeptides that are prone to aggregation in solution. Specifically, certain polypeptides are stable and retain biological activity in a variety of buffer systems, a property which allows skilled artisans to use them in a variety of buffer conditions without considering issues of polypeptide stability. In contrast, other polypeptides fall into a class of macromolecules that have the characteristic of being unstable (e.g. prone to aggregate etc.) to varying degrees in many if not all buffer systems. Consequently practitioners working with polypeptides that are unstable and prone to aggregation in solution can benefit by employing buffer conditions that optimize polypeptide stability in order to retain maximal biological activity.

As illustrated in detail below, the present invention provides a solution formulation which is a physiologically tolerated buffer comprising a mixture of TRIS and a buffer which can absorb $CO_2$ and has no free amine group (such as a phosphate, acetate or citrate buffer etc.). While a number of buffering molecules which can absorb $CO_2$ and have no free amine group are known in the art, throughout this application, a mixed TRIS-phosphate buffer is used as a typical illustrative embodiment of this mixed buffer system. In addition, while the invention applies to a wide variety of polypeptide formulations that can be used in different contexts, it is particularly useful in continuous infusion systems where a device continuously administers a fluid to a patient parenterally for an extended period of time or for, intermittently administering a fluid to a patient parenterally over an extended period of time without having to establish a new site of administration each time the fluid is administered.

The discovery that a mixed buffer system provides enhances polypeptide stability is unexpected in view of art which directs artisans to utilize buffer systems which employ a single buffering component such as TRIS, arginine or phosphate. In addition, discovery that a mixed buffer system provides enhances polypeptide stability is unexpected in view of art which teaches that when physiologically tolerated buffets other than phosphate are employed in formulations of zinc-monomeric insulin analog complexes, protamine salt formulations, or biphasic mixtures of monomeric insulin analog, the physical stability of the formulations is greater than when phosphate buffer is used. For example, art in this field teaches that soluble formulations of zinc monomeric insulin analogs in a phosphate buffer are not physically stable enough for long-term administration using continuous infusion pumping systems and that TRIS buffers without molecules such as phosphate remain stable against aggregation for markedly longer periods of time than do formulations comprising a phosphate buffer (see e.g. WO 98/56406). Without being bound by a specific scientific theory, polypeptides appear to be highly stabilized by the mixed buffer system disclosed herein due to a synergistic interaction between TRIS (which supplies the negative coefficient of pH in combination) and a buffering molecule that can both react with/absorb $CO_2$ (thereby inhibiting the functional impact of this molecule on pH) and has no free amine group (and therefore cannot interact with the insulin molecule through this moiety).

As disclosed herein, when for example, a mixed TRIS-buffer system is employed in formulations of zinc-polypeptide complexes (such as zinc-monomeric insulin analog complexes), protamine salt formulations, or biphasic mixtures of polypeptides, the physical stability of the polypeptides is in fact greater than that observed in buffer systems utilizing either TRIS or other buffers (such as phosphate buffer) alone. Moreover, the soluble formulations provided by the instant invention are sufficiently stable to be used with safety for long periods of insulin infusion and have significant advantages over soluble formulations of zinc monomeric insulin analog complexes with either only TRIS or only phosphate buffer, such as those disclosed in U.S. Pat. No. 5,474,978 and PCT Application WO 98/56406.

Definitions

For purposes of the present invention, as disclosed and claimed herein, the following terms and abbreviations have the following meanings.

The terms "polypeptide" and "protein" are used interchangeably herein and encompass natural, synthetic and recombinant polypeptides having a desired biological activity, including polypeptides and proteins having deleted, replaced or altered amino acid sequences in comparison with the full-length natural polypeptide or biologically active fragments thereof.

The term "complex" means a composition comprising two or more parts, such as a compound in which a transition metal is coordinated to at least one ligand. Ligands include nitrogen-containing molecules, such as proteins, peptides, amino acids, and TRIS, among many other compounds. Monomeric insulin analog can be a ligand of divalent zinc ions.

The various forms of the verb "to aggregate" refer to a process whereby individual molecules or complexes associate to form aggregates. An exemplary aggregate is a polymeric assembly comprising molecules or complex of monomeric insulin analog. Monomeric insulin analogs, and hexamer complexes thereof, have a propensity to aggregate when, for example, they are exposed to thermo-mechanical stress. Aggregation can proceed to the extent that a visible precipitate is formed.

As used herein, the noun "stability" refers to the physical and chemical stability of formulations of polypeptides such as monomeric insulin analogs. Physical instability of a protein formulation may be caused by aggregation of the protein molecules to form higher order polymers or even precipitates. A "stable" formulation is one wherein the degree of aggregation of proteins therein is acceptably controlled, and does not increase unacceptably with time. Monomeric insulin analog formulations have a propensity to aggregate when exposed to thermo-mechanical stress. Physical stability may be assessed by methods well-known in the art, including measurement of a sample's apparent attenuation of light (absorbance, or optical density). Such a measurement of light attenuation relates to the turbidity of a formulation. Turbidity is produced by aggregation or precipitation of proteins or complexes in the formulation. Other methods for assessing physical stability are well-known in the art.

The terms "monomeric human insulin analog", "monomeric insulin analog" and "human insulin analog" are well-known in the art, and refer generally to fast acting analogs of human insulin, which include: human insulin, wherein Pro at position B28 is substituted with Asp, Lys, Leu, Val, or Ala, and wherein position B29 is Lys or is substituted with Pro; AlaB26-human insulin, des(B28–B30) human insulin; and des(B27) human insulin. Such monomenc insulin analogs are disclosed in U.S. Pat. No. 5,514,646, WO 99/64598, WO 99/6459A2 and WO 96/10417A1.

The term "TRIS" refers to 2-amino-2-hydroxymethyl-1,3,-propanediol, and to any pharmacologically acceptable salt thereof. The free base and the hydrochloride form are two common forms of TRIS. TRIS is also known in the art as trimethylol aminomethane, tromethamine, and tris (hydroxymethyl)aminomethane.

The term "arginine" refers to the amino acid and encompasses the D- and L-enantiomers as well as mixtures thereof. The term also includes any pharmacologically acceptable salts thereof. Arginine is also known in the art as 1-amino-4-guanidinovaleric acid.

The term "phenolic preservative" as used herein, typically refers to art accepted phenolic preservatives such as chlorocresol, m-cresol, phenol, or mixtures thereof.

An "isotonicity agent" is a compound that is physiologically tolerated and imparts a suitable tonicity to a formulation to prevent the net flow of water across cell membranes that are in contact with the formulation. Compounds, such as glycerin, are commonly used for such purposes at known concentrations. Other possible isotonicity agents include salts, e.g., sodium chloride, dextrose, and lactose.

The term "administer" means to introduce formulation of the present invention into the body of a patient in need thereof to treat a disease or condition.

The term "continuous infusion system" refers to a device for continuously administering a fluid to a patient parenterally for an extended period of time or for, intermittently administering a fluid to a patient parenterally over an extended period of time without having to establish a new site of administration each time the fluid is administered. The fluid contains a therapeutic agent or agents. The device comprises a reservoir for storing the fluid before it is infused, a pump, a catheter, or other tubing for connecting the reservoir to the administration site via the pump, and control elements to regulate the pump. The device may be constructed for implantation, usually subcutaneously. In such a case, the insulin reservoir will usually be adapted for percutaneous refilling. Obviously, when the device is implanted, the contents of the reservoir will be at body temperature, and subject to the patient's body motion.

The term "treating" refers to the management and care of a patient having a pathology such as diabetes or hyperglycemia, or other condition for which insulin (or other polypeptide) administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

Use of Mixed Buffer Systems in Polypeptide Formulations

While not being bound by a specific theory or mechanism of action, the advantages of the invention are clarified when one examines the main routes of chemical and physical degradation of a representative polypeptide, for example insulin. While insulin is discussed herein as an illustrative molecule, the various factors which contribute to the instability of this molecule also contribute to the instability of a variety of polypeptides. Consequently, the mixed buffer stabilizing formulation disclosed herein can be used with a variety of polypeptides that are prone to chemical and physical degradation.

The chemical stability of insulin is governed by two main reactions, both of which are temperature dependent. The first reaction that occurs in more acidic conditions is the deamidation of the $A^{21}$ and $B^3$ positions. The second main sets of reactions occur at relatively higher pH values and involve changes in the disulfide linkages that define the structure of the insulin molecule. Insulin and its analogs contain three disulfide bonds, two between the A and B chains and one that joins two portions of the A chain. At relatively higher pH values these disulfide linkages can be broken and occasionally scrambled. The molecules that result from disulfide breaking have no biological activity and can lead to further aggregation of insulin in an autocatalytic reaction.

As illustrated above, the physical stability of insulin is governed by two major factors, the presence of any insulin molecules that have had disulfide linkages disrupted or by insulin monomers that have been denatured by contact with hydrophobic surfaces. In this context, physical instability is manifested as aggregation of the insulin (turbidity) and the generation of high molecular weight insulin polymers. Neither the aggregates nor the polymers have insulin biological activity and insulin aggregates have been suggested as potential causes of elevated levels of anti-insulin antibodies.

The invention disclosed herein addresses the above problems associated with polypeptide instability by identifying formulation conditions which provide polypeptides with the combination of chemical and physical stability required for variety of uses such use in a pump infusion system. As described above, thermal reactions occur at both low and higher pH and these changes can give rise to new molecular structures that either have biological potency or not. In this context, the invention disclosed herein provides a formulation that conserves structure at refrigerator temperatures during long term storage (1 to 2 years) and also conserves structure during 90 day pump storage at high temperature and agitation. As illustrated below, the invention disclosed herein utilizes a buffer system that has a relatively high pH at refrigerator temperatures but is lower at body temperature.

Figure 2:
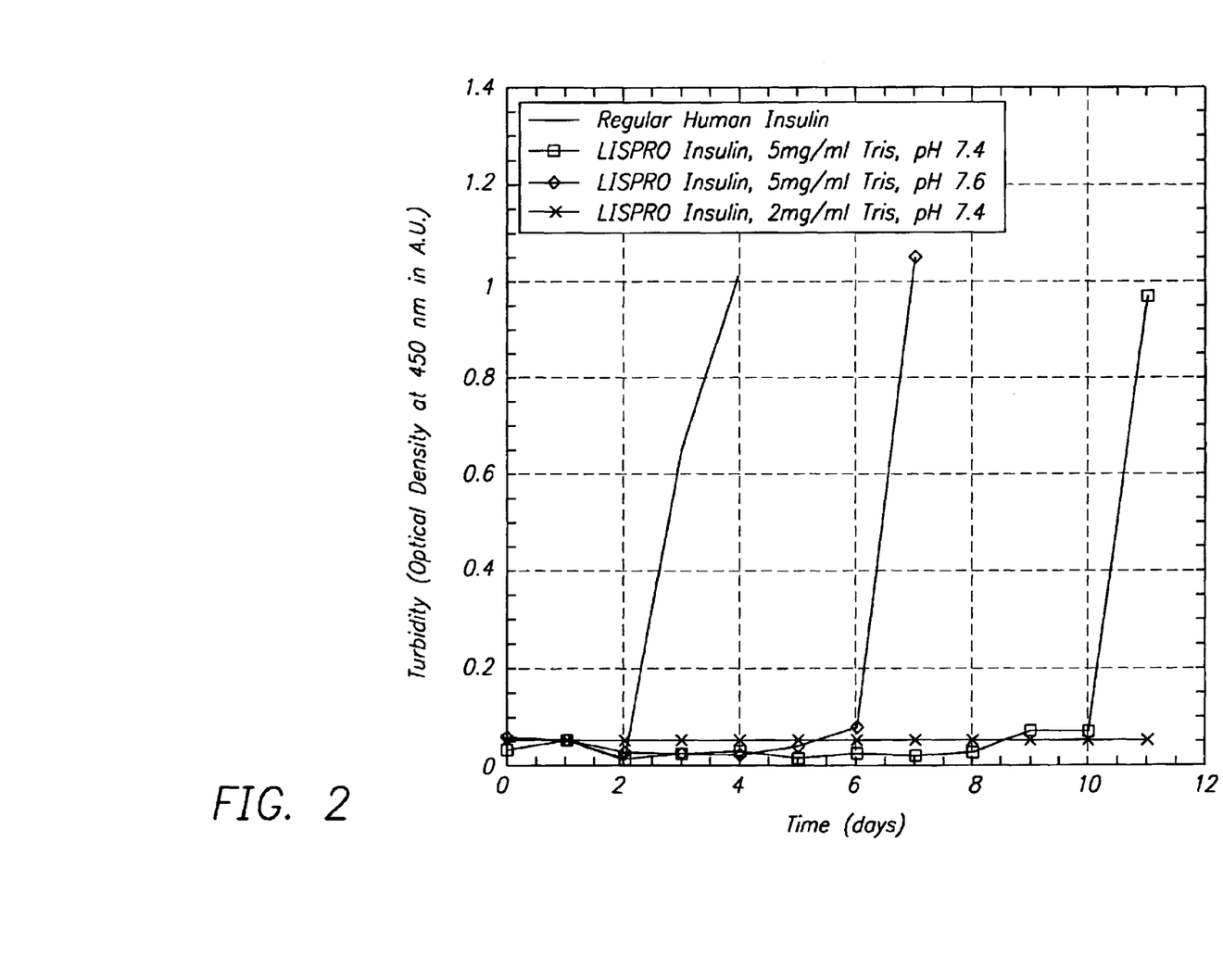
FIG. 2 shows the stability of various insulin formulations and demonstrates the effect of pH and buffer concentration on the physical stability of U400 LISPRO formulations.
Figure 3:
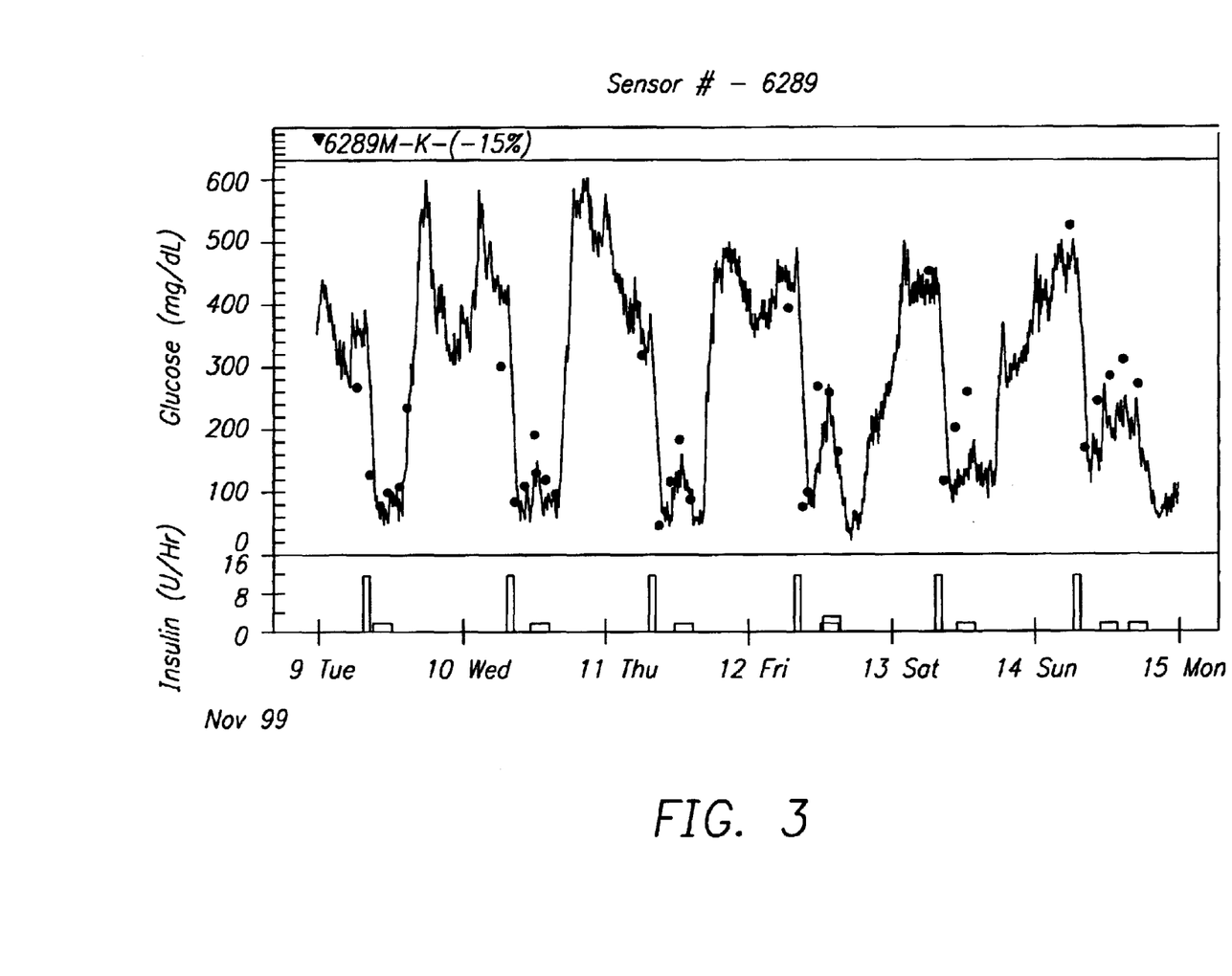
FIG. 3 shows a glycemic response to intraperitoneal delivery of LISPRO insulin. In particular, this figure shows long term glucose sensor data from an IV glucose sensor (MRG). Glucose control using U400 insulin LISPRO in PISCES for more than 90 days. Insulin delivery is shown by red bars.
Figure 4:
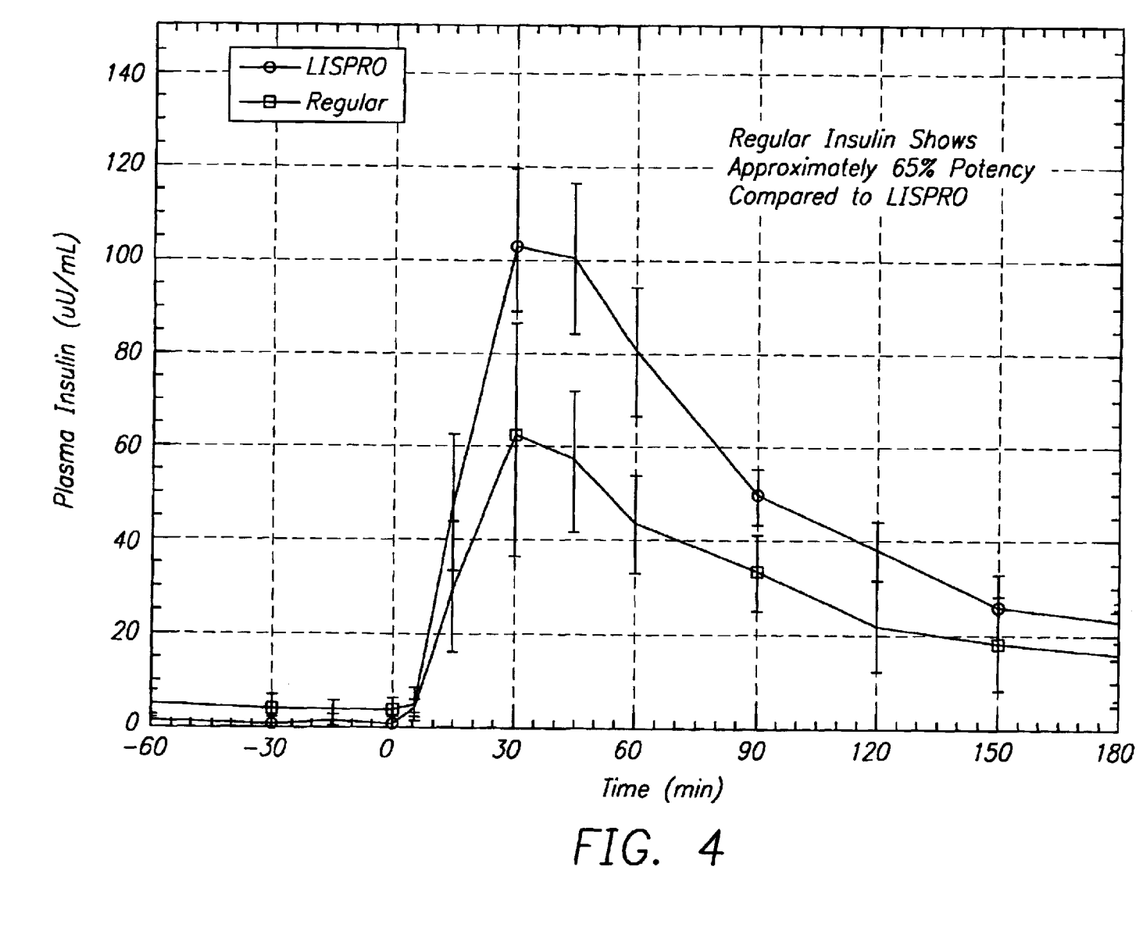
FIG. 4 shows the pharmacokinetics following intraperitoneal administration of LISPRO or regular human insulin. This graph shows that regular insulin has approximately 65% potency as compared to LISPRO.

TRIS buffer, with a temperature coefficient of pH of −0.028 pH/degree C has the appropriate properties for obtaining the chemical and physical stability required for suitable pump use. Therefore a formulation that has a high pH at refrigerator temperature such as 7.7 will have a pH at body temperature of 6.8 or so at 37° C. This is an ideal case and in the case of insulin formulations, the actual pH will be around 6.95 to 6.97 due to the amine terminus of insulin also contributing to the pH effect. Unfortunately, using TRIS alone as a buffer is not ideal and, as shown in FIG. 2, insulin is more stable at lower TRIS concentrations. In particular, the plot shown in FIG. 2 demonstrates the effect of pH and buffer concentration on the physical stability of various insulin formulations including U400 LISPRO formulations. While the exact reasons for this are not clear, TRIS has a significant interaction with zinc ions and that zinc ions stabilize the formulation. Evidence from CD spectra also shows that TRIS in the absence of zinc has a significant interaction with the insulin molecule.

In addition to the concerns with pH, it is impossible to use TRIS at a low concentration because in the body, one must accommodate for $CO_2$ diffusion from the intraperitoneal space (where the catheter is implanted) into the insulin solution, through the walls of the catheter. In a canine model, significant insulin precipitation (enough to block catheters) is observed when using a TRIS concentration of only 2 mg/ml. While the use of 5 mg/ml in the canine model led to no precipitation in the catheter, with this concentration, the insulin stability in the reservoir is compromised.

As disclosed herein, the difficulties of using TRIS alone are overcome through the use of a mixed buffet system. Specifically, by using TRIS to supply the negative coefficient of pH in combination with buffering molecules that: (1) can absorb $CO_2$ and (2) have no free amine group (and thus cannot interact with the insulin molecule through this moiety) a formulation that provides enhanced polypeptide stability is obtained. A variety of such buffeting molecules which have no free amine group and are able to react with $CO_2$ (and thus counteract or offset a deleterious pH change that results from the presence of this molecule) are known in the art (see e.g. "Buffer Solutions: The Basics" (Basics (Oxford England)) by R. J. Beynon and J. S. Eastetby (1996) and "pH and Buffer Theory: A New Approach" (Wiley Series in Solution Chemistry, V.1) by H. Rilbe (1996)). In illustrative embodiments of the invention, one can use TRIS with acetate, phosphate or citrate buffers at the appropriate pH.

Throughout this application, TRIS is identified as an illustrative molecule of choice for use in the disclosed mixed buffer systems. While TRIS may be preferred for used in the disclosed buffer systems, other molecules which function in an analogous manner to TRIS are also contemplated. Specifically, the skilled artisan understands that a wide variety of buffer systems are well known in the art (e.g. TRIS, HEPES, MOPS, PIPES, MES, MOPSO, TAPSO, POPSO, DIPSO, HEPPSO, CAPSO, AMNPSO etc.). In this context, the skilled artisan understands that buffering molecules having like properties can be substituted in circumstances where an equivalent buffering milieu is generated. Consequently, using the disclosure herein, variations on the mixed buffer formulations, such as those which use molecules which function in a manner analogous to TRIS, can readily be generated by the skilled artisan.

The mixed buffers systems of the present invention are specifically designed to address problems in the art related to the destabilization of polypeptides, a phenomena which can be measured by a number of procedures known in the art. For example, a typically unstable polypeptide is IL-2, which destabilizes via at least three pathways: aggregation, methionine oxidation, and deamidation (Kenney et al., "Parameters for the evaluation of IL-2 stability", Lymphokine Research (1986), 5, S23–S27). Several analytical methods are available to monitor IL-2 changes due to physical and chemical destabilizations during storage. A RP-HPLC method (see e.g. Kunitani et al., "Reversed-Phase chromatography of Interleukin-2 muteins", J. of Chromatography, (1986) 359, 391–402), which applies an acetonitrile gradient to elute IL-2 species from a C4 column, is suitable for such analysis. It detects the main IL-2 species as peak B, a methionine oxidative species (mainly oxidized Met-104) as peak A, a deamidated species (probably Asn 88) as peak B' and other unknown species eluting either earlier or later than these peaks. A native SEC-HPLC has also been developed for monomeric IL-2 using isocratic elution with 200 mM ammonium sulfate and a TosoHaas TSK G2000 column. IL-2 elutes as a single species. In addition, a variety of in vitro bioassays can be used to can be used to determine the bioactivity of a molecule such as insulin or IL-2 (e.g. using HT-2 cell proliferation and MTT stain can be used to determine IL-2 bioactivity, Gillis et. al., J. Immuno. 120, 2027–2032 (1978); Watson, J. Exp. Med., 150, 1510–1519 (1979)).

Formulations of the Invention

The invention described herein has a variety of embodiments. An illustrative embodiment consists of a solution formulation consisting of a mixed buffer system of TRIS combined with a buffering molecule which has the property of reacting with carbon dioxide but does not contain a free amine group (and thus is limited in its ability to interact with the polypeptide), the polypeptide, zinc; and a phenolic preservative. In a preferred embodiment of the invention the buffering molecule is selected from the group consisting of acetate, phosphate and citrate. In a highly preferred embodiment, the buffering molecule is phosphate. In a related embodiment of this invention, the formulation further comprises an isotonicity agent and the polypeptide is a monomeric insulin analog selected from the group consisting of LysB28ProB29-human insulin and AspB28 human insulin.

In a specific embodiment of the mixed buffer system described herein, TRIS is present at a concentration of about 1.5 mg/ml to about 4.5 mg/ml; phosphate is present at a concentration of about 0.2 mg/ml to about 2.5 mg/ml, insulin is present at a concentration of about 250 to about 1000 U/ml, zinc is present at a concentration of about 0.07 $\mu$g/ml to about 0.09 $\mu$g/ml, m-cresol is present at a concentration of about 2.2 mg/ml, phenol is present at a concentration of about 0.9 mg/ml and glycerol is the isotonicity agent and is present at a concentration of about 16 mg/ml. In a preferred embodiment, TRIS is present at a concentration of about 2 mg/ml to about 3 mg/ml and phosphate is present at a concentration of about 0.5 mg/ml to about 1.5 mg/ml.

In another typical specific embodiment of the mixed buffer system described herein which uses citrate, TRIS is present at a concentration of about 1.5 mg/ml to about 4.5 mg/ml; citrate is present at a concentration of about 1.5 mg/ml to about 3.0 mg/ml, insulin is present at a concentration of about 250 to about 1000 U/ml, zinc is present at a concentration of about 0.07 µg/ml to about 0.09 µg/ml, m-cresol is present at a concentration of about 2.2 mg/ml, phenol is present at a concentration of about 0.9 mg/ml and glycerol is the isotonicity agent and is present at a concentration of about 16 mg/ml. In a preferred embodiment, TRIS is present at a concentration of about 2 mg/ml and citrate is present at a concentration of about 3.0 mg/ml.

Yet another embodiment of the invention consists of a stable, soluble formulation of a monomeric insulin analog for use in a continuous infusion system, comprising: an isotonicity agent; a mixed buffer system consisting essentially of TRIS combined with a buffer selected from the group consisting of phosphate buffer, acetate buffer and citrate buffer; a monomeric insulin analog; zinc; and a phenolic preservative.

Yet another embodiment of the invention consists of a method for treating diabetes comprising administering an effective dose of the above-mentioned formulation to a patient in need thereof. A related embodiment of the invention consists of a method for treating hyperglycemia comprising administering an effective dose of the disclosed formulation a patient in need thereof. In a preferred embodiments of these methods, the formulation is administered using a continuous infusion system Another embodiment of the invention disclosed herein includes a process for preparing the formulation by combining a physiologically-tolerated mixed buffer system comprising TRIS combined with a buffer selected from the group consisting of phosphate buffer, acetate buffer and citrate buffer; with a polypeptide prone to aggregation; zinc; and a phenolic preservative. In this process, by using TRIS to supply the negative coefficient of pH in combination with a buffer that: (1) can react with $CO_2$ and (2) has no free amine group, a method for providing enhanced polypeptide stability is obtained. A typical embodiment of this method for stabilizing a polypeptide comprises combining TRIS with a buffering molecule which can both react with $CO_2$ and has no free amine group, wherein enhanced polypeptide stability is obtained. In preferred embodiments, the buffer is phosphate buffer. In other illustrative embodiments of the invention, one can use TRIS with acetate or citrate buffers at the appropriate pH. In a variation on such methods, additional stabilizing reagents are added to the formulation. Typically, such reagents include zinc; and a phenolic preservative. In highly preferred embodiments of the invention, the method is used to stabilize an insulin polypeptide.

Using the disclosure provided herein, artisans can employ methods of stabilizing a polypeptide prone to aggregation by combining the peptide with a physiologically-tolerated mixed buffer system comprising TRIS mixed with a buffering molecule that the artisan selects for the characteristics of containing no free amine group and which can counteract the effect that carbon dioxide has on the pH of the formulation containing these interactive components. Typically such methods also include the use of zinc and a phenolic preservative to further stabilize the polypeptide as well as an isotonicity agent such as glycerol. In such methods, the buffering molecule is selected from the group consisting of acetate, phosphate and citrate. While a variety of polypeptides can be stabilized by such methods, in preferred embodiments, the polypeptide is a monomeric insulin analog selected from the group consisting of LysB28ProB29-human insulin and AspB28 human insulin. In a specific embodiment of this method, TRIS is present at a concentration of about 1.5 mg/ml to about 4.5 mg/ml (and preferably of about 2 mg/ml to about 3 mg/ml); phosphate is present at a concentration of about 0.2 mg/ml to about 2.5 mg/ml (and preferably of about 0.5 mg/ml to about 1.5 mg/ml), the monomeric insulin analog is present at a concentration of about 250 to about 1000 U/ml, zinc is present at a concentration of about 0.07 µg/ml to about 0.09 µg/ml, m-cresol is present at a concentration of about 2.2 mg/ml, phenol is present at a concentration of about 0.9 mg/ml and glycerol is the isotonicity agent and is present at a concentration of about 16 mg/ml.

The concentration of monomeric insulin analog in the present formulations ranges from 1.2 mg/ml to 50 mg/ml. A preferred range of analog concentration is from about 3.0 mg/ml to about 35 mg/ml. More preferred concentrations are about 3.5 mg/ml, about 7 mg/ml, about 14 mg/ml, about 17.5 mg/ml, and about 35 mg/ml which correspond approximately to formulations having about 100 units, about 200 units, about 400 units, about 500 units, and about 1000 units of insulin activity per ml, respectively.

The concentration of zinc in the formulations ranges from about 0.5 µg/ml to about 370 µg/ml, and must be such that at least two zinc atoms are available to complex with the six insulin molecules in each hexamer. The ratio of total zinc (complexed zinc plus uncomplexed zinc) to insulin analog hexamer should be between 2 and 4. A ratio of about 3 to about 4 atoms of total zinc per insulin analog hexamer complex is preferred.

The minimum concentration of phenolic preservative that is required to form the monomeric insulin analog hexamer in the present formulations. For some purposes, such as to meet compendial preservative effectiveness requirements for multi-use formulations, the concentration of phenolic preservative in the present formulations may be increased above that required to form hexamers to an amount necessary to maintain preservative effectiveness. The concentration of preservative necessary for effective preservation depends on the preservative used, the pH of the formulation, and whether substances that bind or sequester the preservative are also present. Generally, the amount necessary can be found in, e.g., WALLHAUSER, K. DH., DEVELOP. BIOL. STANDARD. 24, pp. 9–28 (Basel, S. Krager, 1974). When formulated, the insulin analog hexamer complex used in the present formulation binds as many as seven phenolics, though generally, only six phenolics are bound to the hexamer. A minimum of about three phenolics is required for hexamer formation. When preservative is required for anti-microbial effectiveness, the preferred phenolic concentration is about 23 mM to about 35 mM. M-cresol and phenol, either separately or in mixtures, are preferred preservatives.

The formulations may optionally contain an isotonicity agent. The formulations preferably contain an isotonicity agent, and glycerin is the most preferred isotonicity agent. The concentration of glycerin, when it is used, is in the range known in the art for insulin formulations, preferably about 16 mg/ml.

In addition to utilizing a mixed buffer system comprising TRIS in combination with a buffer that: (1) can react with $CO_2$ and (2) has no free amine group, the utilization of additional stabilizers typically used in the art are also contemplated for use in this mixed buffer system. For example, methionine is included in the disclosed pharmaceutical formulations as a means to effectively inhibit the oxidation of methionine residues in the protein. In addition, nonionic surfactants such as polysorbate 80 may be included to inhibit the damage to polypeptides that can occur with freeze-thawing and mechanical shearing. Moreover, EDTA and other known scavengers of metal ions (which are known to catalyze many oxidation reactions), may be added to further stabilize the compositions.

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) may optionally be added to the formulation. These additives are not required to achieve the great advantage of the present invention, but may be useful if the formulations will contact plastic materials.

Administration may be via any route known to be effective by the physician of ordinary skill. Parenteral administration is preferred. Parenteral administration is commonly understood as administration by other than a gastrointestinal route. Preferred parenteral routes for administering the formulations of the present invention include intravenous, intramuscular, subcutaneous, intraperitoneal, intraarterial, nasal, pulmonary, and buccal routes. Intravenous, intraperitoneal, intramuscular, and subcutaneous routes of administration of the compounds used in the present invention are more preferred parenteral routes of administration. Intravenous, intraperitoneal, and subcutaneous routes of administration of the formulations of the present invention yet more highly preferred.

Administration via certain parenteral routes may involve introducing the formulations of the present invention into the body of a patient through a needle or a catheter, propelled by a sterile syringe or some other mechanical device such as an continuous infusion system. A formulation provided by the present invention may be administered using a syringe, injector, pump, or any other device recognized in the art for parenteral administration. A formulation of the present invention may also be administered as an aerosol for absorption in the lung or nasal cavity. The formulations may also be administered for absorption through the mucus membranes, such as in buccal administration.

The amount of a formulation of the present invention that is administered to treat diabetes or hyperglycemia depends on a number of factors, among which are included, without limitation, the patient's sex, weight and age, the underlying causes of the condition or disease to be treated, the route of administration and bioavailability, the persistence of the administered monomeric insulin analog in the body, the formulation, and the potency of the monomeric insulin analog. Where administration is intermittent, the amount per administration should also take into account the interval between doses, and the bioavailability of the monomeric insulin analog from the formulation. Administration of the formulation of the present invention could be continuous. It is within the skill of the ordinary physician to titrate the dose and infusion rate or frequency of administration of the formulation of the present invention to achieve the desired clinical result.

Monomeric insulin analogs used in the present invention can be prepared by any of a variety of recognized peptide synthesis techniques including classical solution methods, solid phase methods, semi-synthetic methods, and recombinant DNA methods. Chance, et al., U.S. Pat. No. 5,514,646, issued May 7, 1996, discloses the preparation of various monomeric insulin analogs with sufficient detail to enable one skilled in the art to prepare any of the monomeric insulin analogs used in the present invention.

Both zinc and a phenolic preservative are used to achieve a complex that is stable and capable of rapid dissociation and onset of action. The hexamer complex consists of two zinc ions per hexamer of human insulin analog, and at least three molecules of a phenolic preservative selected from the group consisting of chlorocresol, m-cresol, phenol, and mixtures thereof. Soluble monomeric insulin analog is converted to the hexamer complex by dissolving the monomeric insulin analog in a diluent containing the phenolic preservative in suitable quantities at a pH of about 7 to about 8 and then adding zinc. Zinc is preferably added as a zinc salt, such as, without limitation, zinc acetate, zinc bromide, zinc chloride, zinc fluoride, zinc iodide, and zinc sulfate. The skilled artisan will recognize that there are many other zinc salts which also might be used to make the monomeric insulin analog complexes that are part of the present invention. Preferably, zinc acetate, zinc oxide, or zinc chloride is used because these compounds do not add new chemical ions to commercially accepted processes.

Dissolution of the monomeric insulin analog may be aided by what is commonly known as "acid dissolution." For acid dissolution, the pH the aqueous solvent is lowered to about 3.0 to 3.5 with a physiologically tolerated acid, preferably HCl, to aid in the dissolution of the monomeric analog. Other physiologically tolerated acids include, without limitation, acetic acid, citric acid, and sulfuric acid. Phosphoric acid is preferably not used to adjust pH in preparing the formulations of the present invention. The pH is then adjusted with a physiologically tolerated base, preferably sodium hydroxide, to about pH 7.3 to 7.5. Other physiologically tolerated bases include, without limitation, potassium hydroxide and ammonium hydroxide. Thereafter, the phenolic preservative and zinc are added.

Parenteral formulations of the present invention can be prepared using conventional dissolution and mixing procedures. To prepare a suitable formulation, for example, a measured amount of monomeric insulin analog in water is combined with the desired preservative, a zinc compound, and the buffering agent, in water in sufficient quantities to prepare the hexamer complex. The formulation is generally sterile filtered prior to administration. Variations of this process would be recognized by one of ordinary skill in the art. For example, the order the components are added, the order in which pH is adjusted, if any, the temperature and ionic strength at which the formulation is prepared, may be optimized for the concentration and means of administration used.

The present invention is further detailed in the following Example, which is offered by way of illustration and are not intended to limit the invention in any manner. All patent and literature references cited in the present specification are hereby incorporated by reference in their entirety.

EXAMPLE 1

The interaction between a protein drug and its delivery system has been of considerable interest for more than 10 years. In particular, the interaction between insulin formulations and implantable pumps have been studied in great detail. During the course of clinical trials using Hoechst U400 insulin and the MiniMed implantable pump system, it has become clear that insulin stability in the implantable pump system is of paramount importance to efficacious glucose control in patients. In 1997, a model of insulin/pump interactions was published that showed the importance of an interaction between the free insulin monomer in the formulation with the surface of the pump (Proceedings of AIDSPIT (Artificial Insulin Delivery Systems, Pancreas and Islet Transplant) meeting, February, 1997). The model is captured in the following equation.

This model provides evidence that as monomeric insulin in solution reaches a surface some of the insulin is irreversibly adsorbed to the surface where it can unfold. Subsequently, the denatured insulin falls off the surface and acts as an autocatalytic agent for the formation of insulin aggregates in solution. These insulin aggregates have been postulated as being immunogenic and the cause of backflow in the pumps (Jeandidier et al.; Diabetologia May 1995; 38(5): 577–84; Lougheed et al., Diabetologia Jul; 1980; 19(1): 1–9).

The availability of insulin LISPRO has given us a potential to test our understanding of insulin/pump interactions with a molecule that has significantly different chemical equilibria than regular human insulin. Several years ago (AIDSPIT 1997) Professor Selam suggested that insulin LISPRO was not suitable for implantable pumps due to the inherent lack of physical stability in LISPRO formulations. The fundamental physical properties of LISPRO suggest that it should be less stable in our model than regular insulin since it has more free monomer at a given concentration. In this context, this example investigates the interactions of insulin LISPRO with implantable pumps and to define the variables that significantly affect the chemical and physical stability of these formulations.

Chemical stability was assessed by measuring the insulin, insulin-related protein, high molecular weight protein, and preservative levels by HPLC. Zinc was measured by inductively coupled plasma spectroscopy.

Physical stability was estimated by continuous agitation of formulations at 37° C., at 40 Hz and 20G (force of gravity) in a custom built apparatus. Insulin was placed in HPLC vials with Teflon balls (4.75 mm diameter) with no air space. Shaking was horizontal and physical stability is estimated by the time for the solutions to turn turbid as measured by optical absorbance at 450 nm.

Phatmacokinetics of insulin and insulin LISPRO formulations were assessed in 6 mongrel dogs made diabetic by full pancreatectomy (2), partial pancreatectomy and Streptozotocin (2), Streptozotocin and Alloxan (1) and Alloxan alone (1). Dogs were subsequently implanted with an implantable pump (MiniMed) filled with either an insulin LISPRO formulation (n=3) or a regular human insulin formulation (n=3). Catheters were placed so that insulin was delivered to the intraperitoneal cavity. On each of two study days, dogs were fasted for 24 hours while continuing a basal rate delivery (0.39–2.0 U/hr). A venous catheter for blood sampling was inserted at t=−1 hour and blood samples were drawn to measure baseline insulin levels. At t=0, a 0.4U/kg bolus was administered by the pump over a 10 minute time interval. Samples for plasma insulin were obtained at −60, −30, −15, 0, 5, 15, 30, 45, 60, 90, 120, 150 and 180 minutes relative to the start of bolus delivery. Samples were analyzed in duplicate by appropriate ELISA techniques (Mercodia).

In-vitro evaluation of insulin formulation stability was obtained by circular dichroism spectroscopy (OLIS), and by fluorescence lifetime spectroscopy (Joban Yvan).

Figure 1:
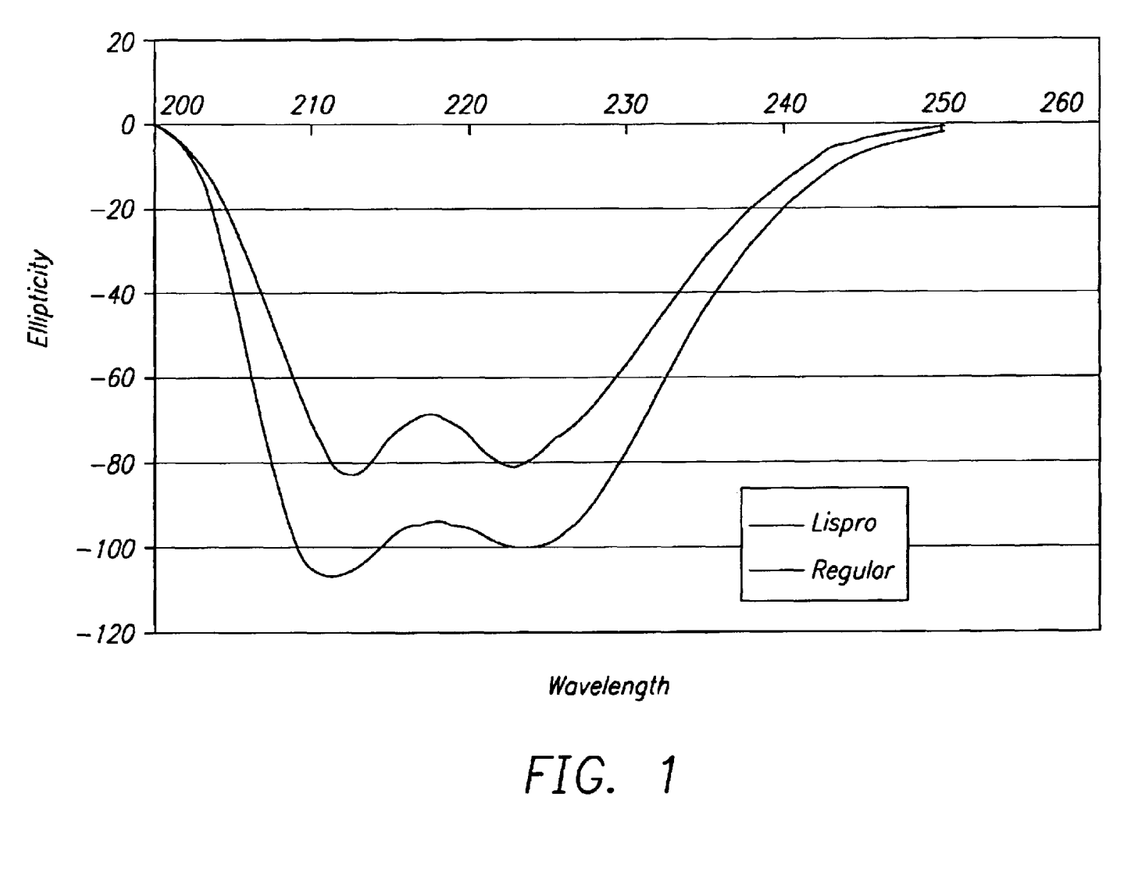
FIG. 1 shows circular dichroism indicating that the conformations of the two types of insulin in similar formulations are the same.

The chromatograms of FIG. 1 illustrate that after 90 days in the implantable pump reservoir, there is no significant change in the amount or type of insulin-related substances. The circular dichroism results indicate that the conformations of the two types of insulin in similar formulations are the same. Fluorescence lifetime measurements were performed. The data obtained indicated that LISPRO insulin has a longer lifetime than regular human insulin.

Physical stability data indicates that LISPRO formulations with a lower concentration of TRIS are more physically stable than formulations with higher TRIS concentrations. It also demonstrates that formulations at lower pH are more physically stable. This information alone, however, does not determine the suitability of a formulation for use in the implantable pump. In-vitro and in-vitro testing of formulations with low buffer concentration and low pH at room temperature demonstrated that the temperature and $CO_2$ concentration found in the canine model led to pH induced precipitation of the LISPRO insulin. An optimum formulation will therefore not necessarily be the one with the best physical stability or the best chemical stability, but one which has the best combination of chemical and physical stability in the conditions for intended use.

The results of the phatmacokinetics study indicate that regular human insuln and LISPRO insulin both peak in the blood following intraperitoneal delivery at the same time, thirty minutes following the start of the bolus. Regular human insulin appears to have approximately 65% of the potency of LISPRO insulin. This may be due to elevated insulin antibody levels in the dogs receiving regular human insulin. Further testing will be performed to explore this and other possibilities.

Many techniques have been developed and used in combination to determine the suitability of an insulin formulation for use in the implantable pump. Testing has demonstrated that concentrating solely on physical or chemical stability alone will not provide an adequate representation of how successful the formulation will be when used with the implantable pump.

What is claimed is:

1. A method of inhibiting aggregation of a polypeptide comprising combining the polypeptide with a buffer comprising tris(hydroxymethyl)aminomethane (TRIS) mixed with a buffering molecule that does not contain a free amine group and which mitigates the change in pH that results from the formation of carbonic acid; zinc; and a phenolic preservative for a time and under conditions effective to inhibit aggregation.

2. The method of claim 1, wherein the buffering molecule is selected from the group consisting of acetate, phosphate and citrate.

3. The method of claim 1, wherein the buffer further comprises an isotonicity agent.

4. The method of claim 1, wherein the polypeptide is a monomeric insulin analog selected from the group consisting of LysB28ProB29-human insulin and AspB28 human insulin.

5. The method of claim 4, wherein TRIS is present at a concentration of about 1.5 mg/ml to about 4.5 mg/ml; phosphate is present at a concentration of about 0.2 mg/ml to about 2.5 mg/ml, the monomeric insulin analog is present at a concentration of about 250 to about 1000 U/ml, zinc is present at a concentration of about 0.07 µg/ml to about 0.09 µg/ml, m-cresol is present at a concentration of about 2.2 mg/ml, phenol is present at a concentration of about 0.9 mg/ml and glycerol is the isotonicity agent and is present at a concentration of about 16 mg/ml.

6. The method of claim 5, wherein TRIS is present at a concentration of about 2 mg/ml to about 3 mg/ml and phosphate is present at a concentration of about 0.5 mg/ml to about 1.5 mg/ml.

7. A method of inhibiting aggregation of a polypeptide consisting essentially of combining the polypeptide with a buffer comprising tris(hydroxymethyl)aminomethane (TRIS) mixed with a buffering molecule selected so that it does not contain a free amine group and which mitigates the change in pH that results from the formation of carbonic acid; zinc; and a phenolic preservative for a time and under conditions effective to inhibit aggregation.

* * * * *